United States Patent
Bejot et al.

(10) Patent No.: US 12,329,830 B2
(45) Date of Patent: Jun. 17, 2025

(54) COMPOSITION CONTAINING A SOMATOSTATIN ANALOGUE FOR RADIOPHARMACEUTICAL USE

(71) Applicant: Ariceum Therapeutics GmbH, Berlin (DE)

(72) Inventors: Romain Bejot, Wrexham (GB); Bilal Karaaoui, Dreux (FR); Didier Kubiak, Dreux (FR); Anne-Claire Le Meur, Dreux (FR); Didier Nourrisson, Dreux (FR); Anne Petit, Dreux (FR); Joel Richard, Dreux (FR); Camille Toulisse, Dreux (FR)

(73) Assignee: Ariceum Therapeutics GmbH, Berlin (DE)

( * ) Notice: Subject to any disclaimer, the term of this patent is extended or adjusted under 35 U.S.C. 154(b) by 731 days.

(21) Appl. No.: 17/251,786

(22) PCT Filed: Jun. 20, 2019

(86) PCT No.: PCT/EP2019/066327
§ 371 (c)(1),
(2) Date: Dec. 12, 2020

(87) PCT Pub. No.: WO2019/243487
PCT Pub. Date: Dec. 26, 2019

(65) Prior Publication Data
US 2021/0128758 A1 May 6, 2021

(30) Foreign Application Priority Data
Jun. 21, 2018 (EP) .................................... 18179054

(51) Int. Cl.
| | |
|---|---|
| *A61K 51/08* | (2006.01) |
| *A61K 47/18* | (2017.01) |
| *A61K 47/26* | (2006.01) |
| *A61K 47/36* | (2006.01) |
| *A61K 51/12* | (2006.01) |

(52) U.S. Cl.
CPC ............ *A61K 51/083* (2013.01); *A61K 47/18* (2013.01); *A61K 47/26* (2013.01); *A61K 47/36* (2013.01); *A61K 51/088* (2013.01); *A61K 51/121* (2013.01); *A61K 51/1241* (2013.01)

(58) Field of Classification Search
CPC ...... A61K 51/088; A61K 47/22; A61K 47/17; A61K 51/1241; A61K 51/121; A61K 9/19; A61K 51/083; A61K 47/36; A61K 47/26

See application file for complete search history.

(56) References Cited

U.S. PATENT DOCUMENTS

| | | |
|---|---|---|
| 6,277,356 B1 | 8/2001 | Albert et al. |
| 2011/0269683 A1 | 11/2011 | Rivier et al. |
| 2020/0316233 A1* | 10/2020 | Garrison ................. A61P 35/00 |

FOREIGN PATENT DOCUMENTS

| | | | |
|---|---|---|---|
| CZ | 287012 B6 * | 8/2000 | ........... A61K 51/083 |
| EP | 3015462 A1 | 5/2016 | |
| WO | 2008048942 A2 | 4/2008 | |
| WO | 2016077061 A2 | 5/2016 | |
| WO | 2018065634 A1 | 4/2018 | |

OTHER PUBLICATIONS

Wild et al., J. Nucl. Med., 2014, 55(8), p. 1248-1252. (Year: 2014).*
CZ-287012-B6, 2000, English translation. (Year: 2000).*
Fani, M., et al., "Unexpected Sensitivity of sst2 Antagonists to N-terminal Radiometal Modifications," J Nucl Med. 2012; 53(9):1481-1489.
Chen, B., et al., "Influence of Histidine on the Stability and Physical Properties of a Fully Human Antibody in Aqueous and Solid Forms," Pharm Res. 2003;20(12):1952-60.
Asti, M., et al., "Development of a Simple Kit-Based Method for Preparation of Pharmaceutical-Grade $^{68}$Ga-DOTATOC," Nucl Med Commun. 2015;36(5):502-10.
Molina, M.D., et al., "Formulation Strategies to Minimize Oxidative Damage in Lyophilized Lipid/DNA Complexes During Storage," J Pharm Sci. 2008; 97(12):5089-5105.
Zamora et al., Applied Radiation and Isotopes, 48: 305-309 (1997).
Dalm, et al.; "SSTR-Mediated Imaging in Breast Cancer: Is There a Role for Radiolabeled Somatostatin Receptor Antagonists?," J Nucl. Med, 2017;58:1609-1614.
Kang, et al., "Rapid Formulation Development of Monoclonal Antibodies," URL: https://bioprocessintl.com/manufacturing/formulation/rapid-formulation-development-for-monoclonal-antibodies/; 2016.
Wang, et al., "Antibody Structure, Instability, and Formulation," Journal of Pharmaceutical Sciences. 2007;96(1):1-20.
ChemBJ, DOTA-JR-11; https://www.chembk.com/en/chem/1039726-31-2; 2015.
Summary of Product Characteristics for "Synthamin 14, 8.5% Amino Acid Intravenous Infusion without Electrolytes": retrieved Oct. 7, 2024 from URL <https://emeaclinicalnutrition.baxter.com/sites/g/files/ebysai2871/files/2021-08/uk-spc-2020-04-00116-0295-clean.pdf>.

* cited by examiner

*Primary Examiner* — Michael G. Hartley
*Assistant Examiner* — Leah H Schlientz
(74) *Attorney, Agent, or Firm* — POLSINELLI PC

(57) ABSTRACT

The present invention relates to a somatostatin analogue composition for radiopharmaceutical use, in particular for diagnostic or therapeutic use. More specifically the somatostatin analogue is a receptor-selective somatostatin peptide antagonist.

21 Claims, 1 Drawing Sheet

COMPOSITION CONTAINING A SOMATOSTATIN ANALOGUE FOR RADIOPHARMACEUTICAL USE

CROSS-REFERENCE TO RELATED APPLICATIONS

Figure 1:
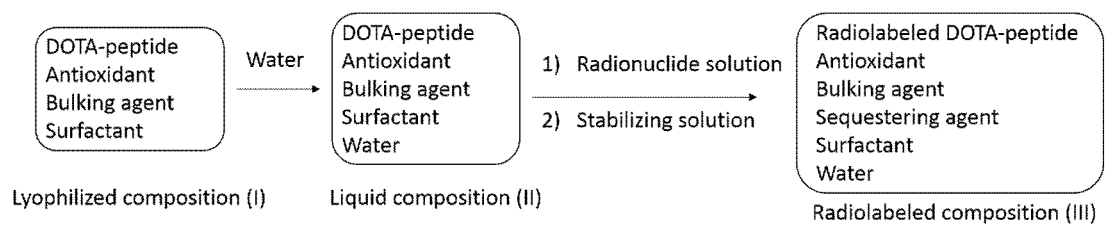

The present application is a 35 U.S.C. § 371 National Stage filing of PCT International Application No. PCT/EP2019/066327, filed Jun. 20, 2019, which claims the priority benefit of European Application No. EP 18179054.4, filed Jun. 21, 2018. The entire contents of each of these applications is incorporated herein by reference.

The present invention relates to a somatostatin analogue composition for radiopharmaceutical use, in particular for diagnostic or therapeutic use. More specifically the somatostatin analogue is a receptor-selective somatostatin peptide antagonist.

The cyclic tetradecapeptide somatostatin-14 (SRIF) affects multiple cellular processes and is also known to inhibit the growth of certain tumors. SRIF induces its biological effects by interacting with a family of membrane-bound structurally similar receptors. Among the five SRIF receptors that have been cloned and are referred to as SSTR1-5, SSTR2 is believed to mediate the inhibition of growth hormone, glucagon and gastric acid secretion. Somatostatin receptors are expressed in pathological states, particularly in neuroendocrine tumors of the gastrointestinal tract and can be identified using in vitro binding methods or using in vivo imaging techniques, the latter allowing the precise localization of the tumors and their metastasis in the patients. Because somatostatin receptors in gastroenteropancreatic tumors are functional, their identification can be used to assess the therapeutic efficacy of an analogue to inhibit excessive hormone release in the patients.

A class of somatostatin peptide analogues which are highly SSTR2 selective and antagonists of somatostatin, although not internalized in cells having SSTR2 receptors, are described in WO 2008/048942. Such peptides bind selectively to cloned SSTR2 without activating the receptor, and these peptide analogues, when iodinated or otherwise radiolabeled, will retain their desirable biological properties. Thus, these peptides are useful in determining the tissue location and cellular expression of the receptor SSTR2.

Thus these peptides can be readily radiolabeled and effectively used in drug screening, imaging, diagnosis and/or radionuclide therapy. For example, these peptides carrying therapeutic radionuclides are useful in radiotherapy, particularly for the treatment of neuroendocrine tumors.

However, there is a need for appropriate formulations for such peptides. Notably there is a need for a formulation having a long shelf-life for handling storage and dispatch, which also enables an efficient radiolabeling of such peptides with radionuclides before administration. There is also a need for a formulation which allows the peptides to remain stable after radiolabeling despite the radiolysis due to the radiation emission from the radionuclides.

The applicant has found a formulation containing such peptides coupled with a chelator, which allows the peptides to remain stable before and after radiolabeling (i.e. after complexation of a radionuclide). After radiolabeling, the role of the formulation is to minimize the degradation caused by radioactive decay of the radionuclides.

By "stable", it is meant in the context of the present invention that the content in peptides is maintained over time. Before radiolabeling, the formulation allows the peptides to remain stable for at least 3 months, preferably at least 12 months, at appropriate storage conditions. After radiolabeling, the formulation allows the peptides to remain stable for at least 7 days at appropriate storage conditions.

The present invention relates to a composition for radiopharmaceutical use, such composition containing at least one receptor-selective somatostatin peptide antagonist, in particular the peptide with an amino acid sequence presented below (INN: satoreotide):

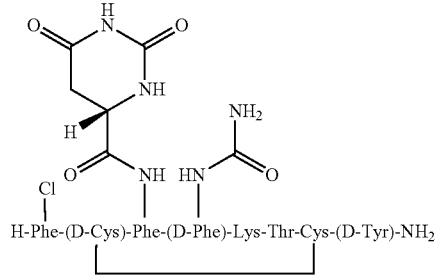

H-Phe-(D-Cys)-Phe-(D-Phe)-Lys-Thr-Cys-(D-Tyr)-NH$_2$

This peptide may directly be coupled at its N-terminus with a chelator, and in particular with the chelator DOTA (1,4,7,10-tetraazacyclododecane-1,4,7,10-tetraacetic acid). Generally, when a percentage or concentration of DOTA-peptide is given, the value is indicated in equivalent free base, even if it is in the form of a salt in the formulation.

The peptide coupled at its N-terminus with chelator DOTA (hereafter called "DOTA-peptide", INN: satoreotide tetraxetan) has the following structure:

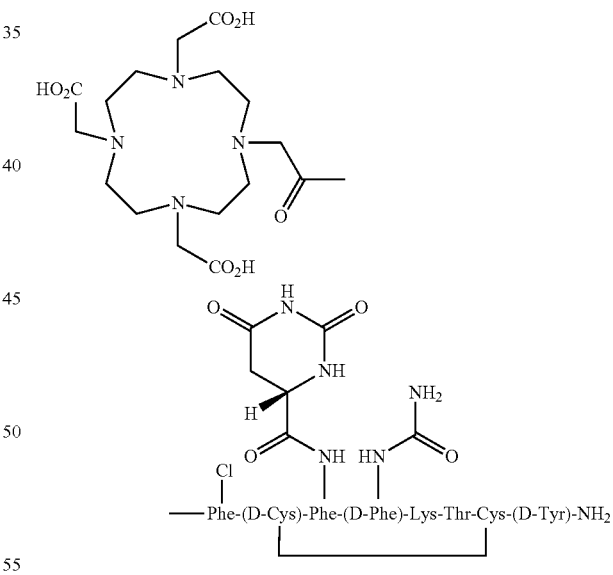

—Phe-(D-Cys)-Phe-(D-Phe)-Lys-Thr-Cys-(D-Tyr)-NH$_2$

DOTA-peptide may be in the form of a salt or a free-base.

DOTA-peptide may be used as a precursor of a radiolabeled compound and thus may be further complexed with or conjugated to an appropriate radionuclide, such as $^{177}$Lu$^{3+}$ cation.

The present invention provides a receptor-selective somatostatin peptide antagonist composition, said composition comprising:
- DOTA-peptide, or a salt thereof, and
- an antioxidant, and
- a bulking agent.

More preferably, the composition of the present invention comprises:
DOTA-peptide, or a salt thereof,
an antioxidant,
a bulking agent,
a buffering agent, and
a surfactant.

In the compositions of the present invention, the bulking agent preferably also has buffering properties. In other words, the bulking agent and the buffering agent are preferably the same excipient. Basic amino acids such as arginine, lysine and histidine are suitable for being bulking agent and buffering agent at the same time.

In the compositions of the present invention, the antioxidant may also have buffering properties. This may notably be the case for ascorbic acid or a salt thereof.

Unless otherwise indicated, the following definitions are set forth to illustrate and define the meaning and scope of the various terms used to describe the invention herein.

Unless otherwise stated, all percentages mentioned in the present invention are weight percentages (w/w).

The term "active ingredient" refers to DOTA-peptide compound described above, eventually complexed with a radionuclide (i.e. radiolabeled).

The term "antioxidant" means a compound having antioxidant properties in order to prevent oxidative degradation reactions, such as redox processes, of the active ingredient and/or the excipients, notably under radiation emission. In particular, it is a free radical scavenger, which traps highly-reactive free radicals, such as oxygen-containing free radicals arising from the radiolysis of water.

The term "bulking agent" as used herein refers to a compound or excipient, which facilitates material handling during a lyophilisation process and enables the formation of a solid cake with a regular surface.

The term "surfactant" as used herein refers to a compound or excipient with surface active properties, used mainly in the present compositions to improve the aqueous solubility of the active ingredient, limit adsorption at solid surfaces and interfaces, help to protect the active ingredient against degradation and/or limit in vitro active ingredient precipitation.

The term "buffering agent" as used herein refers to a weak acid or base used to maintain the pH of a solution near a chosen value after the addition of another acid or base. The function of a buffering agent is to prevent a rapid change in pH when acids or bases are added to a solution or upon dilution, such as when an acidic aqueous solution of radionuclide is added to a solution of DOTA-peptide during the radiolabeling process. The buffering agent also maintains the pH of the composition in the appropriate range to ensure stability and avoid degradation of the DOTA-peptide during processing and storage.

The term "buffer solution" as used herein refers to an aqueous solution containing a mixture of a weak acid and its conjugated base, or vice versa. The pH of a buffer solution changes very little when a small amount of strong acid or base is added to it. When lyophilized, a buffer solution yields the buffering agent or the system of buffering agents.

The term "tonicity agent" as used herein refers to an isotonic modifier or osmotic adjuster (or osmolyte) that provides osmolality to the buffer solution. Osmolality refers to the total osmotic activity contributed by ions and non-ionized molecules to a solution.

The term "solubilizing agent" as used herein means a pharmaceutical excipient used for providing or increasing solubility of the active ingredient in solvent, in particular in water.

The antioxidant may be an antioxidant or a mixture thereof. The antioxidant may be selected from ascorbic acid or a salt thereof, gentisic acid or a salt thereof, methionine, retinol, or ethanol. In a preferred embodiment, the antioxidant is selected from ascorbic acid or a salt thereof, and methionine. More preferably the antioxidant is ascorbic acid or a salt thereof.

The bulking agent may be a bulking agent or a mixture thereof. The bulking agent may be selected from sugar polyols such as mannitol; disaccharides such as sucrose, trehalose or maltose; polysaccharides such as dextrane; cyclodextrines; amino acids such as glycine, arginine, lysine or histidine; and mixtures thereof. In a preferred embodiment, the bulking agent is a basic amino acid, such as arginine, lysine or histidine, and more preferably arginine.

The tonicity agent may be a tonicity agent or a mixture thereof. The tonicity agent may be selected from inorganic salts such as sodium chloride and potassium chloride, mannitol, dextrose, polyethylene glycols (PEGs), polypropylene glycol, glycine, glycerol; and mixtures thereof.

The solubilizing agent may be a solubilizing agent or a mixture thereof. The solubilizing agent may be selected from polyethylene glycols, in particular polyethylene glycol 300 or polyethylene glycol 400, ethanol, propylene glycol, glycerine, polysorbates, in particular polysorbate 20 or polysorbate 80; and mixtures thereof.

The surfactant may be a surfactant or a mixture thereof. Preferably, the surfactant is a non-ionic surfactant. The surfactant may be selected from polysorbates such as polysorbate 20, polysorbate 40, polysorbate 60, polysorbate 80, or a mixture thereof; poloxamers such as poloxamer 188 or mixture thereof. In a preferred embodiment, the surfactant is a polysorbate, also called ethoxylated sorbitan ester of fatty acid. More, preferably, the surfactant is polysorbate 80 (polyoxyethylene (20) sorbitan monooleate).

The salts of DOTA-peptide which can be used for the invention are preferably pharmaceutically acceptable salts of organic acids, such as those of acetic, fumaric, gluconic, alginic, maleic, citric, malic, pamoic, ascorbic, succinic, tartric, or benzoic acids, or pharmaceutically acceptable salts of inorganic acids, such as those of hydrochloric, hydrobromic, hydriodic, sulphuric or phosphoric acids. In a preferred embodiment, DOTA-peptide is in a salt form, and is preferably DOTA-peptide acetate salt.

The term "radiopharmaceutical" is a term well known to a person skilled in the art of nuclear medicine and refers to any chemical or biological agent that comprises a radionuclide having emissions suitable for detection or treatment of malignant diseases. Radiopharmaceuticals may be used for in vivo imaging or for radiotherapy, preferably receptor-targeted radiotherapy.

The compositions of the invention are preferably pharmaceutical compositions, meaning that the excipients and salts described herein are biocompatible excipients and biocompatible salts.

Preferably, the composition of the present invention comprises:
DOTA-peptide, or a salt thereof,
an antioxidant selected from ascorbic acid or a salt thereof;
a bulking agent selected from arginine and histidine, and
a surfactant selected from a polysorbate.

In the above composition, the bulking agent is at the same time a buffering agent.

More preferably, the composition of the present invention comprises:
DOTA-peptide, or a salt thereof,
an antioxidant selected from ascorbic acid or a salt thereof,
a bulking agent which is arginine, and
a surfactant selected from a polysorbate.

Preferably, in the composition of the present invention, the weight ratio of the antioxidant over DOTA-peptide is of at least 20, more preferably comprised from 20 to 60, advantageously comprised from 30 to 50.

Preferably, in the composition of the present invention, the weight ratio of the bulking agent over DOTA-peptide is of at least 15, more preferably comprised from 15 to 45, advantageously comprised from 20 to 35.

Lyophilized Composition

According to a first embodiment, the composition according to the invention is in a lyophilized form, also called "lyophilized composition (I)".

A lyophilized composition (I) according to this embodiment comprises less than 5%, preferably less than 4%, preferably less than 3%, preferably less than 2%, preferably less than 1% by weight of water relative to the total weight of the lyophilized composition.

In order to obtain a radiolabeled formulation ready for radiopharmaceutical use, a lyophilized composition (I) according to this embodiment may be reconstituted with an appropriate reconstitution solution (such as water or a buffer solution) before the addition of a radionuclide in solution.

Preferably, according to this first embodiment, the lyophilized composition (I) of the present invention comprises:
DOTA-peptide, in a salt form,
ascorbic acid or a salt thereof,
arginine, and
a polysorbate.

Preferably, in the lyophilized composition (I), the DOTA-peptide is in a salt form and is present in the range of 0.10% to 3.00% by weight relative to the total weight of the composition, preferably from 0.50% to 2.50%, more preferably from 1.00% to 2.00%.

Preferably, DOTA-peptide in a salt form is present in the range of 1.20% to 1.60% by weight relative to the total weight of the composition.

Preferably, DOTA-peptide is an acetate salt and is present in the lyophilized composition (I) in the range of 1.20% to 1.60% by weight relative to the total weight of the composition.

Preferably, the lyophilized composition (I) comprises an antioxidant present in the range of 40% to 70% by weight relative to the total weight of the composition, preferably from 45% to 65%, more preferably from 50% to 60%.

Preferably, the lyophilized composition (I) comprises ascorbic acid present in the range of 40% to 70% by weight relative to the total weight of the composition, preferably from 45% to 65%, more preferably from 50% to 60%.

Preferably, the lyophilized composition (I) comprises a bulking agent present in the range of 25% to 55% by weight relative to the total weight of the composition, preferably from 30% to 50%, more preferably from 35% to 45%.

Preferably, the lyophilized composition (I) comprises arginine in the range of 25% to 55% by weight relative to the total weight of the composition, preferably from 30% to 50%, more preferably from 35% to 45%.

More preferably, arginine is present in the range of 37% to 43% by weight relative to the total weight of the composition.

Preferably, the lyophilized composition (I) comprises a surfactant present in the range of 0.01% to 0.10% by weight relative to the total weight of the composition, preferably in the range of 0.02% to 0.08%.

Preferably, the lyophilized composition (I) comprises a polysorbate present in the range of 0.01% to 0.10% by weight relative to the total weight of the composition, preferably in the range of 0.02% to 0.08%.

More preferably, the polysorbate is present in the range of 0.05% to 0.07% by weight relative to the total weight of the composition, and more preferably the polysorbate is polysorbate 80.

Preferably, DOTA-peptide, antioxidant, bulking agent and surfactant, taken together, represent at least 95% by weight of the total weight of the lyophilized composition (I), preferably at least 98%, and more preferably at least 99%.

Preferably, in the lyophilized composition (I) of the present invention, the weight ratio of DOTA-peptide over antioxidant is comprised from 1:100 to 1:10, more preferably from 1:80 to 1:20, even more preferably from 1:60 to 1:30.

This ratio enables an efficient protection of the DOTA-peptide against radiolysis when the composition is radiolabeled.

Preferably, according to this first embodiment, the lyophilized composition (I) of the present invention comprises:
DOTA-peptide in a salt form,
ascorbic acid,
arginine, and
a polysorbate,
wherein DOTA-peptide in the salt form, ascorbic acid, arginine and the polysorbate, taken together, represent at least 98% of the total weight of the lyophilized composition.

Preferably, according to this first embodiment, the lyophilized composition (I) of the present invention comprises:
DOTA-peptide acetate salt in the range of 0.10% to 3.00% by weight,
ascorbic acid in the range of 40% and 70% by weight,
arginine in the range of 25% to 55% by weight, and
a polysorbate in the range of 0.01% to 0.10% by weight,
wherein DOTA-peptide acetate salt, ascorbic acid, the disaccharide and the polysorbate, taken together, represent at least 98% of the total weight of the lyophilized composition.

More preferably, the lyophilized composition (I) of the present invention comprises:
DOTA-peptide acetate salt in the range of 0.50% to 2.50% by weight,
ascorbic acid in the range of 45% to 65% by weight,
arginine in the range of 30% to 50% by weight, and
a polysorbate in the range of 0.02% to 0.08% by weight,
wherein DOTA-peptide acetate salt, ascorbic acid, arginine and the polysorbate, taken together, represent at least 98% of the total weight of the lyophilized composition.

More preferably, according to this first embodiment, the dry ingredients of the lyophilized composition (I) of the present invention consist in:
DOTA-peptide acetate salt in the range of 1.20% to 1.60% by weight,
ascorbic acid in the range of 50% to 60% by weight,
arginine in the range of 35% to 45% by weight,
polysorbate 80 in a range of 0.02% to 0.08% by weight.

The lyophilized composition (I) of the invention has the advantage of having a very good stability, meaning that the content of DOTA-peptide is maintained over time. Such a lyophilized composition having an extended shelf-life (of at least 3 months, preferably at least 12 months), it is particularly advantageous for its distribution to the radiopharmacies where it can be reconstituted and radiolabeled before the corresponding radiopharmaceutical drug is administered to the patients.

According to a variant of this first embodiment, the lyophilized composition (I) also comprises one or more additives selected from buffering agents, tonicity agents, and solubilizing agents, which are also under dry or lyophilized form.

In order to obtain a radiolabeled composition ready for radiopharmaceutical use, a lyophilized composition (I) according to the invention may be reconstituted with an appropriate reconstitution solution, such as water for injection, and then mixed under appropriate conditions with a radiolabeling solution, which may be an acidic lutetium-177 chloride solution, such as the one marketed by ITM under the name EndolucinBeta® or the one described in Ph. Eur. Monography 2798: "Lutetium ($^{177}$Lu) solution for radiolabelling".

Preferably, after reconstitution of the lyophilized composition (I), the pH of the mixture is comprised from 3.5 and 5, and preferably between 4.0 and 4.5. This pH is particularly suitable for the radiolabeling of DOTA-peptide with $^{177}$Lu.

Liquid Composition

According to a second embodiment, the composition according to the invention is in a liquid aqueous form, and is called "liquid composition (II)".

The liquid phase of the liquid composition (II) is mainly composed of water. The liquid composition (II) can also be characterized as an aqueous solution wherein the active ingredient and the excipients are solubilized.

A liquid composition (II) according to the present invention may typically be obtained by reconstitution of a lyophilized composition (I) according to the invention with a reconstitution solution, which may be water for injection or a buffer solution.

Preferably, according to this second embodiment, the liquid composition (II) of the invention comprises:
DOTA-peptide, or a salt thereof,
an antioxidant,
a bulking agent, and
water for injection.

Preferably, according to this second embodiment, the liquid composition (II) of the invention comprises:
DOTA-peptide in a salt form,
an antioxidant,
a bulking agent,
a buffering agent,
a surfactant, and
water for injection.

Preferably, according to this second embodiment, the liquid composition (II) of the invention comprises:
DOTA-peptide in a salt form,
ascorbic acid,
arginine,
a polysorbate, and
water for injection.

The following mg/mL concentrations are given in weight relative to the total volume of the liquid composition (II).

Preferably, the liquid composition (II) according to the present invention comprises the DOTA-peptide in a salt form at a concentration of 0.1 to 2.0 mg/mL, preferably at a concentration of 0.25 to 1.75 mg/mL, more preferably at a concentration of 0.5 to 1.5 mg/mL, more preferably at a concentration of 0.75 to 1.25 mg/mL.

More preferably, DOTA-peptide in a salt form is at the concentration of 0.9 to 1.1 mg/mL.

Advantageously, DOTA-peptide is an acetate salt at the concentration of 0.1 to 2.0 mg/mL, 0.25 to 1.75 mg/mL, 0.5 to 1.5 mg/mL, 0.75 to 1.25 mg/mL or 0.9 to 1.1 mg/mL.

Preferably, the liquid composition (II) according to the present invention comprises an antioxidant at a concentration of 20 to 100 mg/mL, preferably at a concentration of 25 to 70 mg/mL, more preferably at a concentration of 30 to 50 mg/mL.

Preferably, the liquid composition (II) according to the present invention comprises ascorbic acid at a concentration of 20 to 100 mg/mL, preferably at a concentration of 25 to 70 mg/mL, more preferably at a concentration of 30 to 50 mg/mL. In a preferred embodiment, ascorbic acid is at the concentration of 35 to 45 mg/mL.

Preferably, the liquid composition (II) according to the present invention comprises a bulking agent at a concentration of 5 to 50 mg/mL, preferably at a concentration of 10 to 40 mg/mL, more preferably at a concentration of 20 to 30 mg/mL.

Preferably, the liquid composition (II) according to the present invention comprises arginine at a concentration of 5 to 50 mg/mL, preferably at a concentration of 10 to 40 mg/mL, more preferably at a concentration of 20 to 30 mg/mL. In a preferred embodiment, arginine is at the concentration of 25 to 30 mg/mL.

Preferably, the liquid composition (II) according to the present invention comprises a surfactant at a concentration of 0.01 to 0.2 mg/mL, preferably at a concentration of 0.02 to 0.1 mg/mL, more preferably at a concentration of 0.03 to 0.05 mg/mL.

Preferably, the liquid composition (II) according to the present invention comprises a polysorbate at a concentration of 0.01 to 0.2 mg/mL, preferably at a concentration of 0.02 to 0.1 mg/mL, more preferably at a concentration of 0.03 to 0.05 mg/mL. In a preferred embodiment, the surfactant is polysorbate 80 at the concentration of 0.03 to 0.05 mg/mL.

Preferably, in the liquid composition (II) of the present invention, the weight ratio of DOTA-peptide over antioxidant is comprised from 1:100 to 1:10, more preferably from 1:80 to 1:20, even more preferably from 1:60 to 1:30.

This ratio enables an efficient protection of the DOTA-peptide against radiolysis when the composition is radiolabeled.

Preferably, according to this second embodiment, the liquid composition (II) of the invention comprises:
DOTA-peptide acetate salt at a concentration of 0.1 to 2.0 mg/mL,
ascorbic acid at a concentration of 20 to 100 mg/mL,
arginine at a concentration of 5 to 50 mg/mL,
a polysorbate at a concentration of 0.01 to 0.2 mg/mL, and
water for injection,
wherein DOTA-peptide acetate salt, ascorbic acid, arginine, the polysorbate and the water for injection, taken together, represent at least 98% by weight of the total weight of the composition.

More preferably, according to this second embodiment, the liquid composition (II) of the invention comprises:
DOTA-peptide acetate salt at a concentration of 0.5 to 1.5 mg/mL,
ascorbic acid at a concentration of 30 to 50 mg/mL,
arginine at a concentration of 20 to 30 mg/mL,
a polysorbate at a concentration of 0.03 to 0.05 mg/mL, and
water for injection, wherein DOTA-peptide acetate salt, ascorbic acid, arginine, the polysorbate and the water for injection, taken together, represent at least 98% by weight of the total weight of the composition.

More preferably, according to this second embodiment, the liquid composition (II) of the invention consists in:
- DOTA-peptide acetate salt at a concentration of 0.9 to 1.1 mg/mL,
- ascorbic acid at a concentration of 35 to 45 mg/mL,
- arginine at a concentration of 25 to 30 mg/mL,
- polysorbate 80 at a concentration of 0.03 to 0.05 mg/mL, and
- water for injection.

Radiolabeled Composition

According to a third embodiment, the composition according to the invention is a radiolabeled composition (III), ready for radiopharmaceutical use.

The radiolabeled composition (III) of the invention is preferably a radiopharmaceutical composition, suitable for injection in mammals.

In a radiolabeled composition (III) according to the invention, the DOTA-peptide is radiolabeled, i.e. complexed with a radionuclide cation.

A radiolabeled composition (III) according to the invention may be obtained by radiolabeling a liquid composition (II) according to the invention.

Alternatively, a radiolabeled composition (III) according to the invention may be directly obtained by radiolabeling of a lyophilized composition (I) according to the invention.

The radiolabeling process is well known by the skilled person in the art and is typically carried out by mixing the liquid composition (II) or the lyophilized composition (I) with a radionuclide cationic salt in solution. Usually, the DOTA-peptide is in molar excess relative to the radionuclide cation, in order to maximize the complexation of the radionuclide cation by the DOTA chelator.

Suitable radionuclides include radionuclides useful in imaging techniques and/or in therapeutic indications.

Suitable radionuclides useful in imaging include, without limitation, the γ-emitting radionuclides for Single Photon Emission Tomography (SPECT) and the positron-emitting radionuclides for Positron Emission Tomography (PET). The γ-emitting radionuclides include, without limitation, $^{67}Ga$, $^{111}In$, $^{177}Lu$, $^{99m}Tc$, and $^{123}I$. The positron-emitting radionuclides include, without limitation, $^{64}Cu$, $^{18}F$, $^{44}Sc$, and $^{68}Ga$.

Suitable nuclides useful in therapeutic indications include, without limitation, the β-emitting radionuclides. Such β-emitting radionuclides may be selected from $^{90}Y$, $^{177}Lu$, and $^{188}Re$.

A preferred radionuclide for the DOTA-peptide active ingredient is a therapeutic radionuclide, and more preferably a therapeutic β-emitting radionuclide. A more preferred therapeutic radionuclide cation is $^{177}Lu^{3+}$.

The radiolabeling process is preferably followed by a step of stabilization consisting of the addition of a stabilizing solution, containing an antioxidant which may be the same (or a salt thereof) as the antioxidant already present in the lyophilized composition (I) or the liquid composition (II). The addition of such stabilizing solution extends the stability of the radiolabeled composition (III) for several days until it is administered to a patient. Such stabilizing solution is particularly useful when $^{177}Lu$ is used as radionuclide in order to prevent radiolysis.

Preferably, according to this third embodiment, the radiolabeled composition (III) of the invention, obtained after radiolabeling and optionally stabilization, comprises:
- radiolabeled DOTA-peptide,
- at least one antioxidant,
- a bulking agent,
- a surfactant,
- water for injection.

Preferably, according to this third embodiment, the DOTA-peptide is complexed with a β-emitting radionuclide, preferably useful in therapy.

Preferably, in the radiolabeled composition (III), the DOTA-peptide is complexed with $^{177}Lu^{3+}$.

Preferably, according to this third embodiment, the radiolabeled composition (III) of the invention also comprises an additional antioxidant, such as sodium ascorbate. Said additional antioxidant may be comprised in the stabilizing solution.

Preferably, according to this third embodiment, the radiolabeled composition (III) of the invention also comprises a sequestering agent, preferably selected from aminocarboxylic acids, edetate disodium, phosphates and phosphonates, polycarboxylates, aminopolycarboxylates, hydroxycarboxylates, sugar acrylates, and mixtures thereof. More preferably, the sequestering agent, is diethylenetriaminepentaacetic acid (DTPA).

Preferably, according to this third embodiment, the radiolabeled composition (III) of the invention comprises:
- $^{177}Lu^{3+}$ radiolabeled DOTA-peptide,
- ascorbic acid and a salt thereof,
- arginine,
- a polysorbate,
- DTPA, and
- water for injection.

More preferably, according to this third embodiment, the radiolabeled composition (III) of the invention comprises and even more consists in:
- $^{177}Lu^{3+}$ radiolabeled DOTA-peptide,
- ascorbic acid and sodium ascorbate,
- arginine,
- a polysorbate,
- DTPA, and
- water for injection.

In the radiolabeled composition (III) according to the present invention, the radiolabeling of DOTA-peptide may not be quantitative. Therefore, the radiolabeled form of DOTA-peptide and the non-radiolabeled form of DOTA-peptide may co-exist in the radiolabeled composition (III) according to the present invention.

Preferably, in a radiolabeled composition (III) according to the present invention, the $^{177}Lu^{3+}$ radiolabeled and non-radiolabeled DOTA-peptide (taken together) is at a concentration comprised from 1 to 100 μg/mL, preferably at a concentration from 10 to 100 μg/mL.

Preferably, the radiolabeled composition (III) according to the present invention comprises an antioxidant or a mixture of antioxidants at a concentration of 10 to 200 mg/mL, more preferably a total concentration of 50 to 150 mg/mL.

Preferably, in a radiolabeled composition (III) according to the present invention, the weight ratio of the DOTA-peptide over the antioxidant is comprised from 1:1500 to 1:10000.

The radiolabeled composition (Ill) according to the present invention preferably comprises, and even more preferably consists in:
$^{177}Lu^{3+}$ radiolabeled DOTA-peptide,
non-radiolabeled DOTA-peptide,
an antioxidant,
a bulking agent,
a surfactant,
a buffering agent,
a sequestering agent, and
optionally one or more pharmaceutically acceptable carriers or diluents.

The radiolabeled composition (III) preferably comprises, and even more preferably consists in:
$^{177}Lu^{3+}$ radiolabeled DOTA-peptide,
non-radiolabeled DOTA-peptide,
a mixture of ascorbic acid and sodium ascorbate,
arginine,
a polysorbate, and
a sequestering agent.

Process of Preparation

The manufacture of the lyophilized composition (I) preferably starts with the manufacture of DOTA-peptide solution which typically consists first in dissolving all the excipients in water for injections. DOTA-peptide is then dissolved in the excipients solution previously prepared, under stirring, until complete dissolution. The bulk DOTA-peptide solution is usually sterilized by sterilizing filtration (for example through a 0.22 μm membrane filter) and then aseptically filled into sterile vials.

Lyophilization may then be carried out according to following procedure. Filled vials are loaded in a freeze dryer and lyophilized following a defined lyophilization cycle, vials are then stoppered under nitrogen in the freeze dryer and finally crimped with an aluminum seal.

The manufacture of the liquid composition (II) uses simple and conventional process unit operations. Water for injection is typically added to a lyophilized composition (I) for reconstitution.

The process for the preparation of the radiolabeled composition (Ill) comprises the complexation (also called radiolabeling) of the DOTA-peptide with a radionuclide in solution and optionally the addition of a stabilizing solution.

The complexation may be performed at room temperature or elevated temperatures by mixing a solution of a radionuclide cation, preferably $^{177}Lu^{3+}$, with the liquid composition (II), at pH between 3.5 and 5, and preferably between 4.0 and 4.5. The complexation of the radionuclide cation, preferably $^{177}Lu^{3+}$, occurs rapidly by the chelator moiety of the DOTA-peptide.

After complexation of the radionuclide, the final mixture can be stabilized by adding a stabilizing solution comprising an antioxidant and optionally a sequestering agent and a surfactant. The antioxidant may also have buffering properties.

During the process, the DOTA-peptide is generally in excess relative to the radionuclide. In particular, during the process of complexation with the radionuclide cation $^{177}Lu^{3+}$, the DOTA-peptide is in excess which gives a ratio $^{177}Lu^{3+}$ radiolabeled DOTA-peptide vs non-radiolabeled DOTA-peptide preferably lower than 1:4.

Kit

Another aspect of the present invention is a kit for the preparation of a radiopharmaceutical composition, said kit comprising at least a suitable container containing a composition as defined above.

In a preferred embodiment, the kit of the invention comprises:
a first vial containing a lyophilized composition (I) as defined above, and
a second vial containing a sterile stabilizing solution.

The stabilizing solution comprises water for injection and an antioxidant. The antioxidant may be selected from ascorbic acid or a salt thereof, gentisic acid or a salt thereof, methionine, retinol, and mixtures thereof.

The stabilizing solution preferably also comprises a buffering agent, which may be selected from acetic acid and its salts, citric acid or its salts, ascorbic acid and its salts, and mixtures thereof. The buffering agent is selected to reach an appropriate pH to ensure that the pH of the radiopharmaceutical composition is within acceptable range for human administration. The buffering agent may at the same time be the antioxidant.

The stabilizing solution preferably comprises an antioxidant, such as sodium ascorbate, according to a concentration (in equivalent ascorbic acid) comprised from 50 to 150 mg/mL, more preferably from 80 mg/mL to 140 mg/mL, even more preferably from 90 mg/mL to 130 mg/mL.

Optionally, the stabilizing solution also comprises a sequestering agent capable to chelate any free radionuclide cation in the mixture. The sequestering agent shall not compete with the DOTA-peptide for complexation of the radionuclide. DTPA (DiethyleneTriaminePentaacetic Acid or Pentetic acid) may be used as a suitable sequestering agent.

The sequestering agent may be comprised at a concentration comprised from 0.01 mg/mL to 1 mg/mL, preferably from 0.05 mg/mL to 0.5 mg/mL.

Optionally, the stabilizing solution also comprises a surfactant, such as a polysorbate, for example polysorbate 80.

The stabilizing solution preferably comprises a surfactant according to a concentration comprised from 0.01 mg/mL to 1 mg/mL, more preferably from 0.1 mg/mL to 0.5 mg/mL.

In a preferred embodiment, the stabilizing solution comprises water for injection, sodium ascorbate (acting as buffering agent and antioxidant), DTPA and polysorbate 80.

The stabilizing solution preferably has a physiological pH, more preferably comprised from 6.0 to 8.0, even more preferably comprised from 6.2 to 7.2.

It was shown that the stabilizing solution advantageously stabilizes a radiolabeled composition (III) obtained from the lyophilized composition (I) of the first vial for a period of at least 7 days.

The role of the stabilizing solution is particularly beneficial in the case where the radiolabeled composition of the invention is a drug radiolabeled with $^{177}Lu^{3+}$. Indeed, since very few radiopharmacies are equipped or allowed to handle lutetium radionuclide, it is not always possible to radiolabel DOTA-peptide with $^{177}Lu^{3+}$ next to the patient bed. Therefore, the radiolabeled drug has to be centrally prepared in a radiopharmacy and then shipped to the different clinical sites where the patients will be treated by administration of the radiolabeled drug. However, the shipment may last for several days and the radiolabeled drug may then be degraded by radiolysis due to the radioactive emission from $^{177}Lu$.

The stabilizing solution thus improves radiochemical stability of the radiolabeled DOTA-peptide, thus extends the shelf-life of the radiolabeled composition and enables the delivery of an appropriate dose of radiolabeled peptide to the patient.

In a preferred embodiment, the kit of the invention comprises:
- a first vial containing a lyophilized composition (I) as defined above, and
- a second vial containing a sterile stabilizing solution comprising water for injection, sodium ascorbate, DTPA and polysorbate 80.

The kit may also contain instructions for mixing the content of the two vials and then complexing with a radionuclide in solution.

The kit of the present invention with the lyophilized composition (I) is advantageously a ready-to-use kit as it can be used with a radionuclide without any addition of further excipients or additives during the preparation of the radiopharmaceutical composition.

Use for Treatment

Another aspect of the present invention is the use of a radiopharmaceutical composition as defined above, for the manufacture of a therapeutic agent for treating a tumor in a mammal.

The peptide as defined above has a selective affinity for SSTR2 receptor, thus a radiopharmaceutical composition as defined above is particularly useful for treating SSTR2 receptor positive tumors, such as neuroendocrine tumors (NETs), and particularly gastroenteropancreatic neuroendocrine tumors (GEP NETs), or tumors of prostate, breast, lung or lymphoma cancer. In a preferred embodiment, a radiopharmaceutical composition as defined above is useful for the manufacture of therapeutic agent for GEP NETs in a mammal.

Method of Treatment

Another aspect of the present invention is a method for treating SSTR2 receptor positive tumors within human body, said method comprising administering to said human an efficient quantity of a radiolabeled composition as defined above.

The radiopharmaceutical composition as defined above may be administered parenterally, preferably intravenously, in the form of injectable solution or suspension, preferably in a single injection. The radiopharmaceutical composition may also be administered by infusion. The appropriate activity may be in the range of 3.0 GBq to 7.4 GBq and a DOTA-peptide dose of 200 μg to 1500 μg.

FIGURES

FIG. 1 schematically represents the process for preparing a radiolabeled composition (III) according to the invention. A lyophilized composition (I) according to the invention is reconstituted with water for injection to provide the liquid composition (II). Then, a radionuclide solution is added to the thereby obtained liquid composition (II), followed by the addition of a stabilizing solution, to provide the radiolabeled composition (III).

Figure 2:
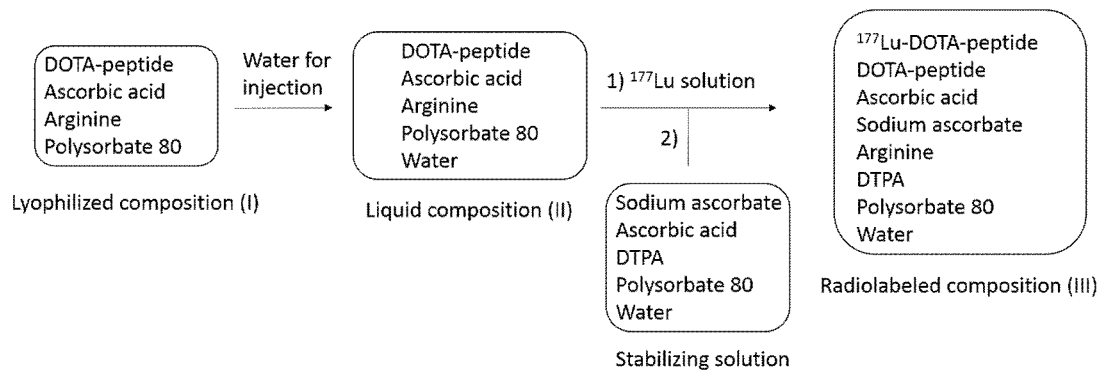

FIG. 2 schematically represents the process for preparing a preferred embodiment of the radiolabeled composition (III) according to the invention. A lyophilized composition (I) according to the invention is reconstituted with water for injection to provide the liquid composition (II). Then, a $^{177}$Lu solution is added to the thereby obtained liquid composition (II), followed by a stabilizing solution, to provide the radiolabeled composition (III).

EXPERIMENTAL PART

Example 1: Preparation of a Lyophilized Composition (I)

71 g of arginine, 100 g of ascorbic acid and 0.1 g of polysorbate 80 were added in a flask containing 900 mL of water for injection (WFI). After dissolution, water for injection was added up to 1 L. 500 mg of pure DOTA-peptide (INN: satoreotide tetraxetan) were weighed and dissolved in 200 mL of the solution previously prepared. The mixture was stirred until complete homogenization and solubilisation of the DOTA-peptide. The solution thus obtained was dispensed in vials (about 10 mg of DOTA-peptide per vial) and lyophilized according to an adequate freeze-drying cycle to get the lyophilized composition (I).

Example 2: Preparation of a Liquid Composition (II)

A lyophilized composition (I) prepared in a vial in example 1 was reconstituted with 10 mL of water for injection in order to reach a liquid composition (II) with a concentration of DOTA-peptide of about 1 mg/mL. The pH of the solution was between 4.0 and 4.5.

Example 3: Preparation of a Stabilizing Composition

A solution was prepared by dissolving 61.87 g of sodium ascorbate (equivalent to 55.00 g of ascorbic acid), 0.05 g of DTPA (pentetic acid) and 0.15 g of polysorbate 80 in 500 mL of water for injection. This solution was sterilized by steam sterilization.

Example 4: Preparation of a Radiolabeled Composition (III)

The liquid composition (II) prepared according to Example 2 was radiolabeled with a diluted lutetium-177 chloride aqueous solution in hydrochloric acid.

Radiolabeling was achieved by preheating the lutetium-177 chloride solution for at least 15 min at 80° C., followed by the addition of the liquid composition (II) of example 2 and immediate heating for 10 min at 80° C. Radiolabeling was performed at a concentration of 0.25 mg/mL of DOTA-peptide.

The mixture was then diluted with the stabilizing composition of example 3 to yield a stock solution of $^{177}$Lu-DOTA-peptide at a concentration of about 1 GBq/mL, which can be divided into individual unit doses for patient administration.

Example 5: Stability Study of the Lyophilized Compositions

Pharmaceutical lyophilized compositions 1 to 6 according to the invention have been prepared according to the process described in example 1, using a total amount of 4 mL of WFI as solvent (then removed via lyophilization) per vial. The amount of the API per vial (i.e. DOTA-peptide in base form) given in Table 1 below is expressed in mg. The percentage of surfactant is given by weight relative to the total weight of dry material.

The stability of these lyophilized compositions (I) has been studied under the different conditions: 40° C./75% RH (RH: relative humidity), 25° C./60% RH, and 5° C. A stability study measures the evolution over time of the amount of API and the evolution over time of the amount of impurities. When the initial amount of API is maintained over time and the amount of impurities does not significantly increase, a pharmaceutical composition is said stable.

TABLE 1

| Lyophilized compositions | API (mg) | antioxidant | bulking agent | surfactant |
|---|---|---|---|---|
| 1 | 10 | ascorbic acid 400 mg | arginine 284 mg | — |
| 2 | 10 | ascorbic acid 400 mg | arginine 284 mg + trehalose 100 mg | polysorbate 80 0.4 mg |
| 3 | 10 | ascorbic acid 400 mg | arginine 284 mg + trehalose 200 mg | polysorbate 80 0.4 mg |
| 4 | 10 | ascorbic acid 400 mg | arginine 284 mg | polysorbate 80 0.4 mg |
| 5 | 10 | ascorbic acid 121 mg + sodium ascorbate 314 mg | dextran 40 284 mg | polysorbate 80 0.4 mg |
| 6 | 10 | ascorbic acid 121 mg + sodium ascorbate 314 mg | arginine 284 mg + trehalose 100 mg | polysorbate 80 0.4 mg |
| 7 | 10 | ascorbic acid 800 mg | arginine 458 mg | — |
| 8 | 10 | ascorbic acid 152 mg + sodium ascorbate 391 mg | dextran 40 400 mg | — |

The stability data at these different conditions and after 2 weeks (2W), 1 month (1M), 2 months (2M), 3 months (3M), 5 months (5M), 6 months (6M) or 12 months (12M) are summarized in Tables 2-4 below. The percentage of impurities is the sum of the percentages of all impurities detected by UPLC (Ultra Performance Liquid Chromatography) and with a percentage over 0.1% (limit of detection). The water content was determined using a coulometer.

TABLE 2 conditions 40° C./75% RH

| | composition 1 | | | | | composition 2 | | | | |
|---|---|---|---|---|---|---|---|---|---|---|
| | T0 | 2 W | 1 M | 2 M | 3 M | T0 | 2 W | 1 M | 2 M | 3 M |
| Water content (%) | 0.99 | — | — | — | — | 1.00 | 1.04 | 1.11 | 1.22 | — |
| API content (mg/vial) | 9.97 | 10.11 | 9.99 | 10.05 | 10.33 | 10.18 | 10.22 | 10.26 | 10.29 | — |
| Impurities (%) | 1.24 | 1.15 | 1.15 | 1.13 | 1.24 | 1.22 | 1.20 | 1.15 | 1.13 | — |

| | composition 3 | | | | | composition 4 | | | | |
|---|---|---|---|---|---|---|---|---|---|---|
| | T0 | 2 W | 1 M | 2 M | 3 M | T0 | 2 W | 1 M | 2 M | 3 M |
| Water content (%) | 1.35 | 1.09 | 1.15 | 1.09 | — | 0.87 | 0.93 | 1.08 | 1.08 | 1.05 |
| API content (mg/vial) | 10.18 | 10.30 | 10.23 | 10.39 | — | 10.26 | 10.52 | 10.47 | 10.51 | 10.77 |
| Impurities (%) | 1.25 | 1.16 | 1.15 | 1.13 | — | 1.36 | 1.20 | 1.16 | 1.13 | 1.21 |

| | composition 5 | | | | | composition 6 | | | | |
|---|---|---|---|---|---|---|---|---|---|---|
| | T0 | 2 W | 1 M | 2 M | 3 M | T0 | 2 W | 1 M | 2 M | 3 M |
| Water content (%) | 2.63 | 2.45 | 2.48 | 2.57 | — | 2.42 | 2.34 | 2.62 | 2.34 | — |
| API content (mg/vial) | 10.21 | 10.45 | 10.16 | 10.29 | — | 9.84 | 10.22 | 10.43 | 10.18 | — |
| Impurities (%) | 1.44 | 1.25 | 1.22 | 1.64 | — | 1.45 | 1.30 | 1.23 | 1.63 | — |

| | composition 7 | | | | | composition 8 | | | | |
|---|---|---|---|---|---|---|---|---|---|---|
| | T0 | 2 W | 1 M | 2 M | 3 M | T0 | 2 W | 1 M | 2 M | 3 M |
| Water content (%) | 1.8 | — | — | — | 3.9 | 5.2 | — | — | — | — |
| API content (mg/vial) | 9.4 | — | 8.8 | 9.0 | 8.6 | 9.1 | — | 9.6 | 9.3 | — |
| Impurities (%) | 0.9 | — | 1.2 | 1.8 | 2.2 | 0.6 | — | 1.2 | 2.3 | — |

TABLE 3 conditions 25° C./60% RH

| | composition 1 | | | | | composition 2 | | | | composition 3 | | | | composition 4 | | | | |
|---|---|---|---|---|---|---|---|---|---|---|---|---|---|---|---|---|---|---|
| | T0 | 1 M | 2 M | 3 M | 6 M | T0 | 1 M | 2 M | 3 M | T0 | 1 M | 2 M | 3 M | T0 | 1 M | 2 M | 3 M | 6 M |
| Water content (%) | 0.99 | — | — | — | 1.02 | 1.00 | 2.42 | 0.94 | — | 1.35 | 1.07 | 1.13 | — | 0.87 | 0.90 | 0.92 | 0.90 | 0.98 |
| API content (mg/vial) | 9.97 | — | 9.96 | 10.40 | 10.26 | 10.18 | 9.84 | 10.31 | — | 10.18 | 10.23 | 10.47 | — | 10.26 | 10.29 | 10.50 | 10.82 | 10.78 |
| Impurities (%) | 1.24 | — | 1.11 | 1.19 | 1.25 | 1.22 | 1.45 | 1.10 | — | 1.25 | 1.14 | 1.10 | — | 1.36 | 1.18 | 1.11 | 1.17 | 1.07 |

| | composition 5 | | | | composition 6 | | | | composition 7 | | | | | composition 8 | | | |
|---|---|---|---|---|---|---|---|---|---|---|---|---|---|---|---|---|---|
| | T0 | 1 M | 2 M | 3 M | T0 | 1 M | 2 M | 3 M | T0 | 1 M | 2 M | 3 M | 5 M | T0 | 1 M | 2 M | 3 M |
| Water content (%) | 2.63 | 2.65 | 2.12 | — | 2.42 | 2.39 | 2.29 | — | 1.8 | — | — | 4.0 | 2.3 | 5.2 | — | — | — |
| API content (mg/vial) | 10.21 | — | 10.23 | — | 9.84 | — | 10.19 | — | 9.4 | 8.9 | 9.1 | 8.8 | 9.2 | 9.1 | 9.7 | 9.4 | — |
| Impurities (%) | 1.44 | — | 1.13 | — | 1.45 | — | 1.13 | — | 0.9 | 0.7 | 0.9 | 1.0 | 1.2 | 0.6 | 0.9 | 1.0 | — |

TABLE 4 conditions 5° C.

| | composition 1 | | | | composition 2 | | | composition 3 | | | composition 4 | | | | |
|---|---|---|---|---|---|---|---|---|---|---|---|---|---|---|---|
| | T0 | 1 M | 3 M | 6 M | T0 | 1 M | 3 M | T0 | 1 M | 3 M | T0 | 1 M | 3 M | 6 M | 12 M |
| Water content (%) | 0.99 | — | — | 0.94 | 1.00 | 0.84 | — | 1.35 | 1.09 | — | 0.87 | 0.82 | 0.90 | 0.85 | 0.75 |
| API content (mg/vial) | 9.97 | — | 10.34 | 10.33 | 10.18 | — | — | 10.18 | — | — | 10.26 | — | 10.82 | 10.82 | 10.52 |
| Impurities (%) | 1.24 | — | 1.23 | 1.08 | 1.22 | — | — | 1.25 | — | — | 1.36 | — | 1.33 | 1.26 | 1.06 |

| | composition 5 | | | composition 6 | | | composition 7 | | | | composition 8 | | |
|---|---|---|---|---|---|---|---|---|---|---|---|---|---|
| | T0 | 1 M | 3 M | T0 | 1 M | 3 M | T0 | 1 M | 3 M | 5 M | T0 | 1 M | 3 M |
| Water content (%) | 2.63 | 2.51 | — | 2.42 | 2.56 | — | 1.8 | 3.2 | 1.7 | 1.7 | 5.2 | 4.7 | 5.1 |
| API content (mg/vial) | 10.21 | — | — | 9.84 | — | — | 9.4 | 8.9 | 8.8 | 9.5 | 9.1 | 9.8 | 9.5 |
| Impurities (%) | 1.44 | — | — | 1.45 | — | — | 0.9 | 0.7 | 1.0 | 1.1 | 0.6 | 0.9 | 0.9 |

Example 6: Stability Study of the Radiolabeled Composition

A pharmaceutical radiolabeled composition 7 according to the invention has been prepared according to the process described in example 4.

After dilution with the stabilizing solution, the radiolabeled composition 7 contained 20 μg/mL of DOTA-peptide (0.6 GBq/mL), 100 mg/mL of ascorbic acid, 0.6 mg/mL of arginine, 0.03% by weight of polysorbate 80, and 0.05 mg/mL of DTPA. The percentage of surfactant is given by weight relative to the total weight of dry material.

The stability of the radiolabeled composition 7 has been studied at room temperature. The total mass content of impurities and the mass contents of the 2 main impurities (A and B), at the end of preparation (T0), after 1 day (1D), 2 days (2D), 4 days (4D), and 7 days (7D) were obtained by HPLC and are summarized in Table 5 below:

TABLE 5

| | T0 | 1 D | 2 D | 4 D | 7 D |
|---|---|---|---|---|---|
| Total impurity (%) | 2.0 | 2.5 | 3.5 | 4.0 | 6.1 |
| Impurity A (%) | < | < | 0.3 | 0.3 | 0.6 |
| Impurity B (%) | < | 0.5 | 1.1 | 1.5 | 2.7 |

<: not detected or % below the limit of qualification

The invention claimed is:

1. A receptor-selective somatostatin peptide antagonist composition comprising:
   a DOTA-peptide of Formula (I)

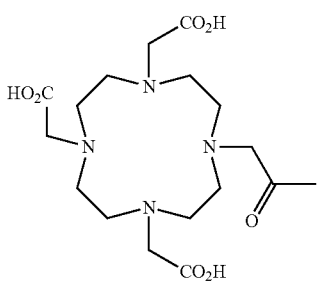

-continued

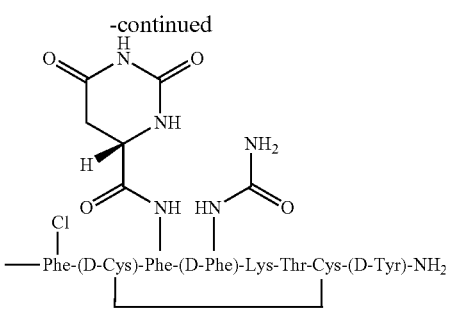

——Phe-(D-Cys)-Phe-(D-Phe)-Lys-Thr-Cys-(D-Tyr)-NH₂ or a salt thereof,
an antioxidant, and
a bulking agent, wherein the bulking agent is arginine, and wherein the weight ratio of the arginine over the DOTA-peptide is of from 15:1 to 45:1.

2. The composition of claim 1, further comprising:
a buffering agent, and
a surfactant.

3. The composition of claim 1, wherein the weight ratio of the antioxidant over the DOTA-peptide is at least 20:1.

4. The composition of claim 1, wherein:
the antioxidant is ascorbic acid or a salt thereof, and
the composition further comprises a surfactant, wherein the surfactant is a polysorbate.

5. The composition of claim 1, wherein the composition is in a lyophilized form.

6. The composition of claim 5, wherein the DOTA-peptide is in a salt form and is present in the range of 0.10% to 3.00% by weight relative to the total weight of the composition.

7. The composition of claim 5, wherein the antioxidant is ascorbic acid and is present in the range of 40% to 70% by weight relative to the total weight of the composition.

8. The composition of claim 5, wherein arginine is present in the range of 25% to 55% by weight relative to the total weight of the composition.

9. The composition of claim 5, further comprising a surfactant, wherein the surfactant is polysorbate 80 and is present in the range of 0.01% to 0.10% by weight relative to the total weight of the composition.

10. The composition of claim 5, comprising:
DOTA-peptide acetate salt in the range of 0.10% to 3.00% by weight;
ascorbic acid in the range of 40% to 70% by weight;
arginine in the range of 25% to 55% by weight; and
a polysorbate in the range of 0.01% to 0.10% by weight;
wherein the DOTA-peptide acetate salt, ascorbic acid, arginine, and the polysorbate, taken together, represent at least 98% of the total weight of the composition.

11. The composition of claim 1, wherein the composition is in a liquid aqueous form.

12. The composition of claim 11, wherein the composition comprises:
a polysorbate and water for injection,
and wherein the antioxidant comprises ascorbic acid or a salt thereof,
and the DOTA-peptide is in a salt form.

13. The composition of claim 11, wherein the DOTA-peptide is in a salt form and is present at a concentration of 0.1 to 2.0 mg/ml.

14. The composition of claim 1, wherein the composition is a radiolabeled composition.

15. The composition of claim 14, wherein the composition comprises:
a polysorbate;
DTPA; and water for injection,
and wherein the antioxidant comprises ascorbic acid or a salt thereof,
and the DOTA-peptide is $^{177}Lu^{3+}$ radiolabeled.

16. A kit comprising a suitable container containing the composition of claim 1.

17. The kit of claim 16 comprising:
a first vial containing the composition, wherein the composition is in a lyophilized form; and
a second vial containing a sterile stabilizing solution comprising an antioxidant.

18. The kit of claim 17, wherein the sterile stabilizing solution comprises water for injection, sodium ascorbate, DTPA and polysorbate 80.

19. A method for treating SSTR2 receptor positive tumors comprising administering to a mammal in need of such treatment an efficient quantity of the composition of claim 14.

20. The method of claim 19, wherein the tumor is selected from: neuroendocrine tumors (NETs) and tumors of prostate, breast, lung or lymphoma cancer.

21. The method of claim 19, wherein the tumor is a gastroenteropancreatic neuroendocrine tumor (GEP NET).

* * * * *